US011110179B2

(12) United States Patent
Kennedy et al.

(10) Patent No.: US 11,110,179 B2
(45) Date of Patent: Sep. 7, 2021

(54) COMBINATION OF CD33 ANTIBODY DRUG CONJUGATES WITH CHEMOTHERAPEUTIC AGENTS

(71) Applicant: Seagen Inc., Bothell, WA (US)

(72) Inventors: Dana Kennedy, Kirkland, WA (US); Eric Feldman, Shoreline, WA (US)

(73) Assignee: Seagen Inc., Bothell, WA (US)

( * ) Notice: Subject to any disclaimer, the term of this patent is extended or adjusted under 35 U.S.C. 154(b) by 124 days.

(21) Appl. No.: 16/306,118

(22) PCT Filed: Jun. 2, 2017

(86) PCT No.: PCT/US2017/035793
§ 371 (c)(1),
(2) Date: Nov. 30, 2018

(87) PCT Pub. No.: WO2017/210621
PCT Pub. Date: Dec. 7, 2017

(65) Prior Publication Data
US 2019/0134215 A1 May 9, 2019

Related U.S. Application Data

(60) Provisional application No. 62/345,644, filed on Jun. 3, 2016, provisional application No. 62/507,560, filed on May 17, 2017.

(51) Int. Cl.
*A61K 47/68* (2017.01)
*A61K 31/5517* (2006.01)
*C07K 16/28* (2006.01)
*A61K 31/704* (2006.01)
*A61K 31/7068* (2006.01)
*A61P 35/02* (2006.01)

(52) U.S. Cl.
CPC ...... *A61K 47/6803* (2017.08); *A61K 31/5517* (2013.01); *A61K 31/704* (2013.01); *A61K 31/7068* (2013.01); *A61K 47/6867* (2017.08); *A61P 35/02* (2018.01); *C07K 16/2803* (2013.01); *C07K 2317/24* (2013.01)

(58) Field of Classification Search
None
See application file for complete search history.

(56) References Cited

U.S. PATENT DOCUMENTS

| | | |
|---|---|---|
| 7,419,811 B2 | 9/2008 | Lavie et al. |
| 7,695,716 B2 | 4/2010 | Drachman et al. |
| 8,337,855 B2 | 12/2012 | Hoffee et al. |
| 8,455,622 B2 | 6/2013 | McDonagh et al. |
| 9,061,074 B2 | 6/2015 | Carter et al. |
| 9,079,958 B2 | 7/2015 | Konopitzkly et al. |
| 9,352,006 B2 | 5/2016 | Chen |
| 9,550,833 B2 | 1/2017 | Konopitzky et al. |
| 9,587,019 B2 | 3/2017 | Sutherland et al. |
| 2002/0022031 A1 | 2/2002 | Goldenberg et al. |
| 2004/0152632 A1 | 8/2004 | Feingold |
| 2007/0190060 A1 | 8/2007 | Boghaert et al. |
| 2008/0104734 A1 | 5/2008 | Kay et al. |
| 2010/0158909 A1 | 6/2010 | McDonagh et al. |
| 2010/0278779 A1 | 11/2010 | Zeldis |
| 2011/0206700 A1 | 8/2011 | Hoffee et al. |
| 2011/0300139 A1 | 12/2011 | Kumar et al. |
| 2012/0082670 A1 | 4/2012 | Konopitzky et al. |
| 2012/0251554 A1 | 10/2012 | Bachmann et al. |
| 2013/0024177 A1 | 1/2013 | Nolan |
| 2013/0028919 A1 | 1/2013 | Howard et al. |
| 2013/0058919 A1 | 3/2013 | Lazar et al. |
| 2013/0109644 A1 | 5/2013 | MacBeth et al. |
| 2013/0309223 A1 | 11/2013 | Sutherland et al. |
| 2014/0011215 A1 | 1/2014 | Albitar et al. |
| 2014/0086942 A1 | 3/2014 | Carter et al. |
| 2014/0335549 A1 | 11/2014 | Albitar et al. |
| 2015/0125447 A1 | 5/2015 | Heider |
| 2015/0147316 A1* | 5/2015 | Sutherland .............. A61P 35/00 424/133.1 |
| 2016/0096892 A1* | 4/2016 | Brogdon ................. A61P 43/00 424/93.21 |
| 2017/0204180 A1 | 7/2017 | Sutherland et al. |
| 2019/0076549 A1 | 3/2019 | Arthur et al. |
| 2019/0117787 A1 | 4/2019 | Kennedy et al. |
| 2019/0262354 A1 | 8/2019 | Arthur et al. |

FOREIGN PATENT DOCUMENTS

| | | | |
|---|---|---|---|
| CA | 2733223 | A1 | 2/2010 |
| EP | 2625201 | B1 | 9/2016 |
| WO | 2004043461 | * | 5/2004 |
| WO | WO2004/043344 | A2 | 5/2004 |
| WO | WO2004/043461 | A1 | 5/2004 |
| WO | WO2008/070593 | A2 | 6/2008 |
| WO | WO2008/070593 | A3 | 6/2008 |
| WO | WO2011/106389 | A1 | 9/2011 |
| WO | WO2011/130613 | A1 | 10/2011 |

(Continued)

OTHER PUBLICATIONS

Alavardo et al., Cancer Chemother Pharmacol (2003) 51: 87-90 (Year: 2003).*
Fenton et al., Drugs 2005; 65 (16): 2405-2427 (Year: 2005).*
Almagro, et al., "Humanization of antibodies", Frontiers in Bioscience 13, pp. 1619-1633, (Jan. 1, 2008).
American Cancer Society, "Typical Treatment of Acute Myeloid Leukemia (Except APL)", Available at: https://www.cancer.org/cancer/acute-myeloid-leukemia/treating/typical-treatment-of-aml.html, 7 pages, (2019).
Balaian, et al., "5-Azacytidine Augments the Cytotoxicity of Mylotarg toward AML Blasts in Vitro and in Vivo", Blood, 110(11), 1835, (Nov. 2007).
Barthelemy, et al., "Comprehensive Analysis of the Factors Contributing to the Stability and Solubility of Autonomous Human $V_H$ Domains", The Journal of Biological Chemistry, vol. 283, No. 6, pp. 3639-3654, (Feb. 8, 2008).

(Continued)

Primary Examiner — Karl J Puttlitz
(74) Attorney, Agent, or Firm — Seagen Inc.

(57) ABSTRACT

This invention relates to treatment of cancer using a CD33 antibody drug conjugate in combination with chemotherapeutic agents.

12 Claims, No Drawings

Specification includes a Sequence Listing.

(56) References Cited

FOREIGN PATENT DOCUMENTS

| WO | WO2012/045752 A1 | 4/2012 |
| --- | --- | --- |
| WO | WO2013/173496 A2 | 11/2013 |
| WO | WO2014/165119 A1 | 10/2014 |
| WO | WO2015/067570 A2 | 5/2015 |
| WO | WO2015/067570 A3 | 5/2015 |
| WO | WO2017/160954 A1 | 9/2017 |
| WO | WO2017/180768 A1 | 10/2017 |
| WO | WO2017/210621 A1 | 12/2017 |
| WO | WO2017/214433 A1 | 12/2017 |

OTHER PUBLICATIONS

Beiboer, et al., "Guided Selection of a Pan Carcinoma Specific Antibody Reveals Similar Binding Characteristics yet Structural Divergence Between the Original Murine Antibody and its Human Equivalent", J. Mol. Biol. 296, pp. 833-849, (2000).

Biddle-Snead, et al., "Assessment of myeloblast CD33 receptor occupancy (RO) by vadastuximab talirine in patients with acute myeloid leukemia (AML) receiving monotherapy treatment", Cancer Research. Proceedings: AACR Annual Meeting 2017, 77(13 supplement), Abstract CT120, (2017).

Bixby, et al., "Vadastuximab Talirine Monotherapy in Older Patients with Treatment Naive CD33-Positive Acute Myeloid Leukemia (AML)", Blood, 128(22):590, (2016).

Casset, et al., "A peptide mimetic of an anti-CD4 monoclonal antibody by rational design", Biochemical and Biophysical Research Communications, 307:198-205, (2003).

Chen, et al., "Selection and Analysis of an Optimized Anti-VEGF Antibody: Crystal Structure of an Affinity-matured Fab in Complex with Antigen", J. Mol. Biol., 293:865-881, (1991).

Choi, et al., "Predicting antibody complementarity determining region structures without classification", Mol. BioSyst., 7, pp. 3327-3334, (2011).

ClinicalTrials.gov, "A Safety Study of SGN-CD33A in Combination With Standard-of-care in Patients With AML", 8 pages, Available at: https://clinicaltrials.gov/cl2/history/NCT02326584?term+33a&draw+2&rank+4, (May 8, 2018).

ClinicalTrials.gov, "A Safety Study of SGN-CD33A in Combination With Standard-of-care in Patients With AML", 6 pages, Available at: https://clinicaltrials.gov/ct2/history/NCT02326584?A+19&B=19&C+merged#StudyPageTop, (May 30, 2016).

ClinicalTrials.gov, "A Safety Study of SGN-CD33A in Combination With Standard-of-care in Patients With AML", 6 pages, Available at: https://clinicaltrials.gov/ct2/history/NCT02326584?A=27&B=27&C=merged#StudyPageTop, (Jan. 19, 2017).

ClinicalTrials.gov, "A Safety Study of SGN-CD33A in Combination With Standard-of-care in Patients With AML", 6 pages, Available at: https://clinicaltrials.gov/ct2/history/NCT02326584?A=30&B=30&C=merged#StudyPageTop, (May 8, 2018).

De Genst, et al., "Antibody repertoire development in camelids", Developmental and Comparative Immunology, 30, pp. 187-198, (2006).

Dombret et al., "An update of current treatments for adult acute myeloid leukemia", Blood, vol. 127, No. 1, pp. 53-61, (Jan. 2016).

Drachman, et al., "The next generation of ADCs", Proceedings: AACR 106th Annual Meeting 2015, Cancer Res. 75 (15 Suppl), Abstract SY35-01 (2015).

EPO Application No. 13790467.8 (Published as EP2850104), European Search Report and European Search Opinion, 7 pages, (dated Jun. 14, 2016).

EPO Application No. 18171884.2, European Search Report and European Search Opinion, 7 pages, (dated Nov. 23, 2018).

EPO Application No. 17807611.3, European Supplementary Search Report and Search Opinion, 8 pages, (dated Dec. 18, 2019).

Erba, et al., "A Phase 1b Study of Vadastuximab Talirine in Combination with 7+3 Induction Therapy for Patients with Newly Diagnosed Acute Myeloid Leukemia (AML)", Blood, 128(22), Abstract No. 211, (2016).

Erba, et al., "SGN-CD33A: case reports of anti-leukemic activity and bridge to allogeneic stem cell transplant (SCT) in patients with acute myeloid leukemia (AML)", Biol. Blood Marrow Transplant 21, (suppl 2), S185-186, (2015).

Feldman, et al, Phase III Randomized Multicenter Study of a Humanized Anti-CD33 Monoclonal Antibody, Lintuzumab, in Combination With Chemotherapy, Versus Chemotherapy Alone in Patients With Refractory or First-Relapsed Acute Myeloid Leukemia, Journal of Clinical Oncology, vol. 23, No. 18, pp. 4110-4116, (Jun. 20, 2005).

Feldman, et al., "Novel Therapeutics for Therapy-Related Acute Myeloid Leukemia: 2014", Clinical Lymphoma, Myeloma & Leukemia, vol. 15, No. S1, pp. S91-S93, (2015).

Griffiths, et al., "Human anti-self antibodies with high specificity from phage display libraries", The EMBO Journal, vol. 12, No. 2, pp. 725-734, (1993).

Jeffrey, et al., "Development of Pyrrolobenzodiazepine-Based Antibody-Drug Conjugates for Cancer", AACR Annual Meeting, Abstract No. 4321, 1 pages, (2013).

Kennedy, et al., "SGN-CD33A: Preclinical and phase 1 interim clinical trial results of a CD33-directed PBD dimer antibody-drug conjugate for the treatment of acute myeloid leukemia (AML)", Proceedings: AACR 106th Annual Meeting 2015, AACR; Cancer Res. 75 (15 Suppl), Abstract DDT02-04, (Apr. 2015).

Kimka, et al., "Human anti-CD30 recombinant antibodies by guided phage antibody selection using cell panning", British Journal of Cancer, 83(2), pp. 252-260, (2000).

Kung Sutherland, et al., "SGN-CD33A: a novel CD33-directed antibody-drug conjugate, utilizing pyrrolobenzodiazepine dimers, demonstrates preclinical antitumor activity against multi-drug resistant human AML", ASH Annual Meeting Abstracts 120: Abstract 3589, (2012).

Kung Sutherland, et al., "SGN-CD33A: a novel CD33-targeting antibody-drug conjugate using a pyrrolobenzodiazepine dimer is active in models of drug-resistant AML", Blood, 122:1455-1463, (2013).

Lamminmaki, et al., "Protein Structure and Folding: Crystal Structure of a Recombinant Anti-estradiol Fab Fragment in Complex with 17β-Estradiol", J. Biol. Chem., 276: 36687-36694, (2001).

Laszlo, et al., "Cellular determinants for preclinical activity of a novel CD33/CD3 bispecific T-cell engager (BiTE) antibody, AMG 330, against human AML", Blood, vol. 23, No. 4, 554-561, (Jan. 23, 2014).

Levy, et al., "A Phase 1b Study of the Combination of Vadastuximab Talirine and 7+3 Induction Therapy for Patients With Newly Diagnosed Acute Myeloid Leukemia (AML)", Proceedings of the 22nd Congress of the European Hematology Association Madrid Spain, Abstract No. S793, (Jun. 25, 2017).

MacCallum, et al., "Antibody-antigen Interactions: Contact Analysis and Binding Site Topography", J. Mol. Biol., 262:732-745, (1996).

Nand, et al., "A phase 2 trial of azacitidine and gemtuzumab ozogamicin therapy in older patients with acute myeloid leukemia", Blood, 122:3432-3439, (2013).

Padlan, et al., "Structure of an antibody-antigen complex: Crystal structure of the HyHEL-10 Fab-lysozyme complex", Proc. Natl. Acad. Sci. USA, 86:5938-5942, (1989).

Othus, et al., "Prediction of CR following a second course of '7+3' in patients with newly diagnosed acute myeloid leukemia not in CR after a first course", Leukemia, 30, pp. 1779-1780, (2016).

Pascalis et al., "Grafting of "Abbreviated" Complementarity-Determining Regions Containing Specificity-Determining Residues Essential for Ligand Contact to Engineer a Less Immunogenic Humanized Monoclonal Antibody", J. Immunol., 169:3076-3084, (2002).

PCT Application No. PCT/US2013/041209, International Preliminary Report on Patentability, 7 pages, (dated Apr. 30, 2015).

PCT Application No. PCT/US2013/041209, International Search Report and Written Opinion, 10 pages, (dated Oct. 25, 2013).

PCT Application No. PCT/US2017/022472, International Preliminary Report on Patentability, 8 pages, (dated Sep. 27, 2018).

PCT Application No. PCT/US2017/022472, International Search Report and Written Opinion, 16 pages, (dated Jul. 19, 2017).

(56) References Cited

OTHER PUBLICATIONS

PCT Application No. PCT/US2017/027246, International Preliminary Report on Patentability, 8 pages, (dated Oct. 25, 2018).
PCT Application No. PCT/US2017/027246, International Search Report and Written Opinion, 14 pages, (dated Jul. 10, 2017).
PCT Application No. PCT/US2017/035793, International Preliminary Report on Patentability, 7 pages, (dated Dec. 13, 2018).
PCT Application No. PCT/US2017/035793, International Search Report and Written Opinion, 9 pages, (dated Sep. 6, 2017).
PCT Application No. PCT/US2017/036605, International Preliminary Report on Patentability, 11 pages, (dated Dec. 20, 2018).
PCT Application No. PCT/US2017/036605, International Search Report and Written Opinion, 20 pages, (dated Oct. 27, 2017).
Rudikoff, et al., "Single amino acid substitution altering antigen-binding specificity", Proc. Natl. Acad. Sci. USA, 79:1979, (1982).
Seattle Genetics, Inc., Press Release, "Seattle Genetics Presents Phase 1b Data from Vadastuximab Talirine (SGN-CD33A; 33A) in Combination with Standard of Care in Frontline Acute Myeloid Leukemia at ASH Annual Meeting", Available at: https://investor.seattlegenetics.com/press-releases/news-details/2016/Seattle-Genetics-Presents-Phase-1b-Data-from-Vadastuximab-Talirine-SGN-CD33A-33A-in-Combination-with-Standard-of-Care-in-Frontline-Acute-Myeloid-Leukemia-at-ASH-Annual-Meeting/default.aspx, 4 pages, (Dec. 3, 2016).
Seattle Genetics, Inc., Press Release, "Seattle Genetics Discontinues Phase 3 CASCADE Trial of Vadastuximab Talirine (SGN-CD33A) in Frontline Acute Myeloid Leukemia", Available at: https://investor.seattlegenetics.com/press-releases/news-details/2017/Seattle-Genetics-Discontinues-Phase-3-CASCADE-Trial-of-Vadastuximab-Talirine-SGN-CD33A-in-Frontline-Acute-Myeloid-Leukemia/default.aspx, 3 pages, (Jun. 19, 2017).
Seiter, "Acute Myeloid Leukemia Treatment Protocols", Medscape, Available at: https://emedicine.medscape.com/article/2004793-print, 7 pages, (2019).
Stein, et al., "A phase 1 trial of SGN-CD33A as monotherapy in patients with CD33-positive acute myeloid leukemia (AML)", Blood, 126(23), Abstract 324, (Dec. 3, 2015).
Stein, et al., "A phase 1 trial of vadastuximab talirine as monotherapy in patients with CD33-positive acute myeloid leukemia", Blood, vol. 131, No. 4, pp. 387-396, (Jan. 25, 2018).
Stein, et al., "Interim analysis of a phase 1 trial of SGN-CD33A in patients with CD33-positive acute myeloid leukemia (AML)", Blood 124(21), Abstract 623, (2014).
Stein, et al., "SGN-CD33A (Vadastuximab Talirine) followed by Allogeneic Hematopoietic Stem Cell Transplant (AlloHSCT) Results in Durable Complete Remissions (CRs) in Patients with Acute Myeloid Leukemia (AML)", Abstracts—Biol Blood Marrow Transplant 22 (suppl 3), pp. 211-212, (2016).
Sutherland, et al., "5-azacytidine enhances the anti-leukemic activity of lintuzumab (SGN-33) in preclinical models of acute myeloid leukemia", mAbs, 2:4 440-448, (2010).
Sutherland, et al., "Anti-leukemic activity of lintuzumab (SGN-33) in preclinical models of acute myeloid leukemia", mAbs, 1:5, 481-490, (2009).
Sutherland, et al., "SGN-CD33A in combination with cytarabine or hypomethylating agents demonstrates enhanced anti-leukemic activity in preclinical models of AML", Blood, 124(21), Abstract No. 3739, (2014).
Tarlock, et al., "2723 Synergistic Effect of SGN-CD33A and FLT3 Inhibitors in FLT3/ITD Acute Myeloid Leukemia", Oral and Poster Abstracts No. 2723, ASH Annual Meeting, 2 pgs., (Dec. 2, 2018).
Tarlock, et al., "3942 CD33 SNP Genotype and Splice Variation are Associated with CD33 Cell Surface Expression and SGN-CD33A Pharmacokinetics", Oral and Poster Abstracts No. 3942, ASH Annual Meeting, 2 pgs., (Dec. 3, 2018).
U.S. Appl. No. 13/804,227, Advisory Action dated Nov. 18, 2015.
U.S. Appl. No. 13/804,227, Final Office Action dated Aug. 10, 2015.
U.S. Appl. No. 13/804,227, Non-Final Office Action dated Feb. 18, 2016.
U.S. Appl. No. 13/804,227, Non-Final Office Action dated Feb. 27, 2015.
U.S. Appl. No. 13/804,227, Non-Final Office Action dated Mar. 14, 2016.
U.S. Appl. No. 13/804,227, Restriction Requirement dated Sep. 18, 2014.
U.S. Appl. No. 13/826,007, Non-Final Office Action dated Sep. 11, 2015.
U.S. Appl. No. 14/401,837, Non-Final Office Action dated May 27, 2016.
U.S. Appl. No. 14/401,837, Notice of Allowance dated Oct. 14, 2016.
Vajdos, et al., "Comprehensive Functional Maps of the Antigen-binding Site of an Anti-ErbB2 Antibody Obtained with Shotgun Scanning Mutagenesis", J. Mol. Biol., 320:415-428, (2002).
Walter, et al., "A Phase 1b Study of Vadastuximab Talirine (33A) in Combination with 7+3 Induction Therapy for Patients with Newly Diagnosed Acute Myeloid Leukemia (AML)", Ann. Hematol. 96, Suppl 1, p. 69, (2017).
Wang, et al., "CASCADE: A phase 3, randomized, double-blind study of vadastuximab talirine (33A) versus placebo in combination with azacitidine or decitabine in the treatment of older patients with newly diagnosed acute myeloid leukemia (AML)", Journal of Clinical Oncology 35, No. 15 suppl, Abstract TPS7066, 1 pg. (2017).
Ward, et al., "Binding activities of a repertoire of single immunoglobulin variable domains secreted from *Escherichia coli*", Nature, vol. 341, pp. 544-546, (Oct. 12, 1989).
Wu, et al., "Humanization of a Murine Monoclonal Antibody by Simultaneous Optimization of Framework and CDR Residues", J. Mol. Biol., 294:151-162, (1999).
Yang, et al., "A Phase 1b Study of Vadastuximab Talirine as Maintenance and in Combination with Standard Consolidation for Patients with Acute Myeloid Leukemia (AML)", Blood, 128(22), Abstract No. 340, (2016).

\* cited by examiner

COMBINATION OF CD33 ANTIBODY DRUG CONJUGATES WITH CHEMOTHERAPEUTIC AGENTS

CROSS-REFERENCES TO RELATED APPLICATIONS

This application is a U.S. national stage filing under 35 U.S.C. § 371 of International Application No. PCT/US2017/035793, filed Jun. 2, 2017, which claims the benefit of U.S. Provisional Application No. 62/345,644 filed Jun. 3, 2016 and U.S. Provisional Application No. 62/507,560 filed May 17, 2017, all of which are hereby incorporated by reference in their entirety for all purposes.

REFERENCE TO A SEQUENCE LISTING

A sequence listing designated 0033-00612PC Sequence Listing.ST25.txt of 15 KB created May 19, 2017, is incorporated herein by reference.

FIELD OF THE INVENTION

This invention relates to treatment of cancer using a CD33 antibody drug conjugate in combination with chemotherapeutic agents.

BACKGROUND OF THE INVENTION

CD33 is a 67 kDa plasma membrane protein that binds to sialic acid and is a member of the sialic acid-binding Ig-related lectin (SIGLEC) family of proteins. CD33 is known to be expressed on myeloid cells. CD33 expression has also been reported on a number of malignant cells. A clinical trial of a CD33 antibody drug conjugate, comprising an h2H12 antibody conjugated to a PBD molecule, has been initiated. Additional improvements in treatment of CD33 expressing cancers are being sought. The present invention solves these and other problems.

BRIEF SUMMARY OF THE INVENTION

This disclosure provides a method of treating a CD33 expressing cancer by administering a CD33 antibody drug conjugate (ADC) using an induction consolidation method. The CD33-ADC comprises a humanized 2H12 antibody and a PBD cytotoxic agent. The variable region sequences of the h2h12 antibody are SEQ ID NOs:1 and 2. The induction consolidation method includes administration of the CD33-ADC in combination with cytarabine and an anthracycline antibiotic or an anthracenedione, e.g., daunorubicin, doxorubicin, idarubicin or mitoxantrone. The CD33 expressing cancer is acute myeloid leukemia (AML).

The PBD cytotoxic agent has the formula

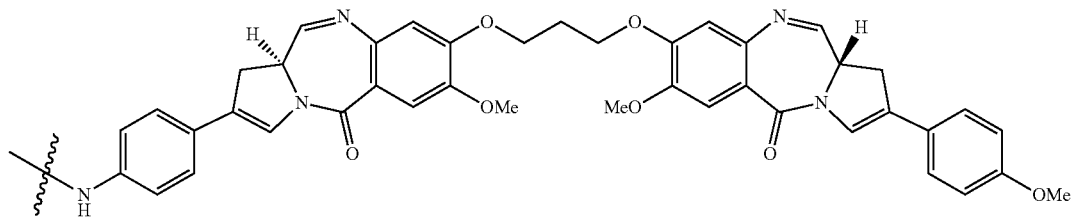 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

A formula of the h2H12 antibody conjugated to the PBD molecule, including a linker has the formula

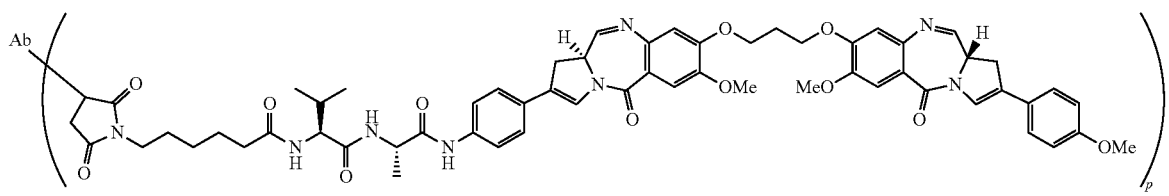

where h2H12 is denoted Ab.

For induction-consolidation, the CD33-ADC is administered at a concentration of 10 μg/kg or 20 μg/kg. For maintenance therapy, the CD33-ADC is administered at a concentration of 5 μg/kg.

This disclosure provides an induction method of treating CD33 expressing acute myeloid leukemia (AML) in a patient by administering cytarabine, an anthracycline antibiotic, and a CD33 antibody drug conjugate (ADC). The CD33-ADC comprises a humanized 2H12 antibody and a PBD cytotoxic agent. The humanized 2H12 antibody includes a light chain variable region of SEQ ID NO:1 and a heavy chain variable region of SEQ ID NO:2. The antibody is an IgG1 isotype and the constant region includes an S239C substitution, using the EU index of Kabat. The PBD cytotoxic agent has the formula

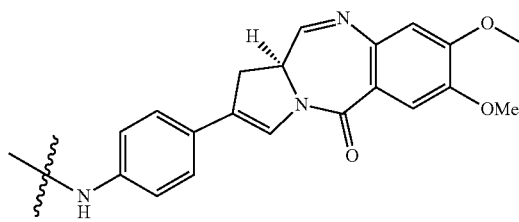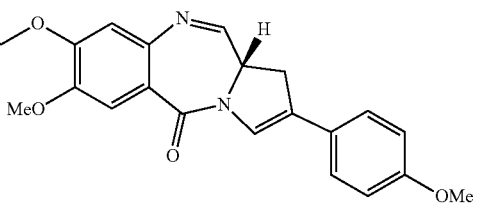

and is conjugated to the antibody at the S239C residues of the constant region. The induction cycle is a seven-day cycle. On day one of the induction cycle 20 μg/kg of the CD33-ADC is administered and on day four of the induction cycle 10 μg/kg of the CD33-ADC is administered. The anthracycline antibiotic is daunorubicin and is administered at 60 mg/m$^2$/day on induction days 1-3 of the induction cycle. Cytarabine is administered to the patient at 100 mg/m$^2$/day on induction days 1-7.

This disclosure provides an induction method of treating CD33 expressing acute myeloid leukemia (AML) in a patient by administering cytarabine, an anthracycline antibiotic, and a CD33 antibody drug conjugate (ADC). The CD33-ADC comprises a humanized 2H12 antibody and a PBD cytotoxic agent. The humanized 2H12 antibody includes a light chain variable region of SEQ ID NO:1 and a heavy chain variable region of SEQ ID NO:2. The antibody is an IgG1 isotype and the constant region includes an S239C substitution, using the EU index of Kabat. The PBD cytotoxic agent has the formula

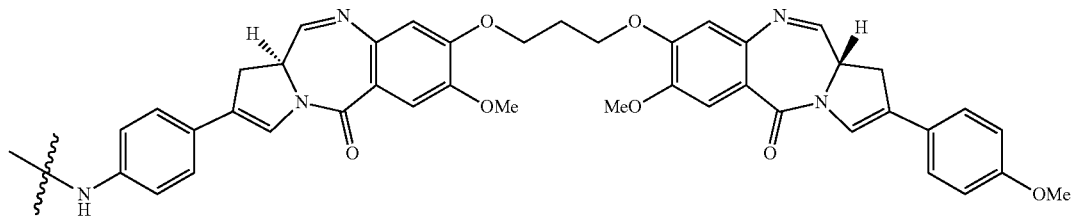 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

and is conjugated to the antibody at the S239C residues of the constant region. The induction cycle is a seven-day cycle. On day one of the induction cycle, 30 μg/kg of the CD33-ADC is administered to the patient. The anthracycline antibiotic is daunorubicin and is administered at 60 mg/m$^2$/day on induction days 1-3 of the induction cycle. Cytarabine is administered to the patient at 100 mg/m$^2$/day on induction days 1-7.

This disclosure provides an induction method of treating CD33 expressing acute myeloid leukemia (AML) in a patient by administering cytarabine, an anthracycline antibiotic, and a CD33 antibody drug conjugate (ADC). The CD33-ADC comprises a humanized 2H12 antibody and a PBD cytotoxic agent. The humanized 2H12 antibody includes a light chain variable region of SEQ ID NO:1 and a heavy chain variable region of SEQ ID NO:2. The antibody is an IgG1 isotype and the constant region includes an S239C substitution, using the EU index of Kabat. The PBD cytotoxic agent has the formula

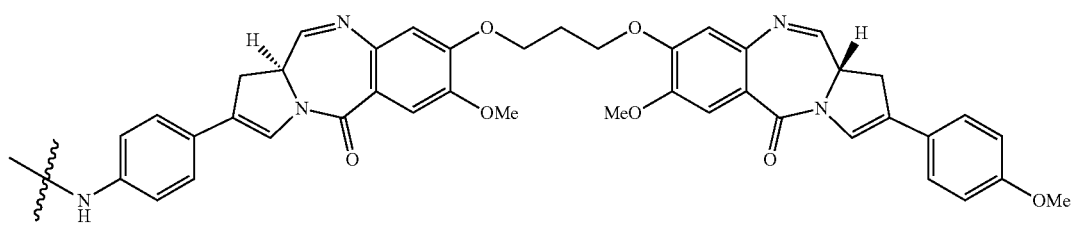 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

and is conjugated to the antibody at the S239C residues of the constant region. The induction cycle is a seven-day cycle. On day one of the induction cycle, 40 µg/kg of the CD33-ADC is administered to the patient. The anthracycline antibiotic is daunorubicin and is administered at 60 mg/m$^2$/day on induction days 1-3 of the induction cycle. Cytarabine is administered to the patient at 100 mg/m$^2$/day on induction days 1-7.

Definitions

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" is used herein to denote immunoglobulin proteins produced by the body in response to the presence of an antigen and that bind to the antigen, as well as antigen-binding fragments and engineered variants thereof. Hence, the term "antibody" includes, for example, intact monoclonal antibodies comprising full-length immunoglobulin heavy and light chains (e.g., antibodies produced using hybridoma technology) and antigen-binding antibody fragments, such as F(ab')2 and Fab fragments. Genetically engineered intact antibodies and fragments, such as chimeric antibodies, humanized antibodies, single-chain Fv fragments, single-chain antibodies, diabodies, minibodies, linear antibodies, multivalent or multispecific (e.g., bispecific) hybrid antibodies, and the like are also included. Thus, the term "antibody" is used expansively to include any protein that comprises an antigen-binding site of an antibody and is capable of specifically binding to its antigen.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics such as, e.g., complement fixation, interaction with cells, and other effector functions. Typically, changes in the variable region will be made in order to improve the antigen-binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, J. Mol. Recog. 12:131-140, 1999; Nguyen et al., EMBO J. 19:921-930, 2000) or from VH domains of other species to produce single-domain antibodies ("dAbs"; see Ward et al., Nature 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., Nature 362: 367-369, 1993; Qiu et al., Nature Biotechnol. 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, Biochem. 31:1579-1584, 1992), a non-peptide linker, an oligonucleotide (see Chaudri et al., FEBS Letters 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')2, F(ab)c, diabodies, dAbs, minibodies, nanobodies, Fab-scFv fusions, bispecific (scFv)4-IgG, and bispecific (scFv)2-Fab. (See, e.g., Hu et al., Cancer Res. 56:3055-3061, 1996; Atwell et al., Molecular Immunology 33:1301-1312, 1996; Carter and Merchant, Curr. Opin. Biotechnol. 8:449-454, 1997; Zuo et al., Protein Engineering 13:361-367, 2000; and Lu et al., J. Immunol. Methods 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function, see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 Kd or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally *Fundamental Immunology* (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The term "chimeric antibody" refers to an antibody having variable domains derived from a first species and constant regions derived from a second species. Chimeric immunoglobulins or antibodies can be constructed, for example by genetic engineering, from immunoglobulin gene segments belonging to different species. The term "humanized antibody," as defined infra, is not intended to encompass chimeric antibodies. Although humanized antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "humanized VH domain" or "humanized VL domain" refers to an immunoglobulin VH or VL domain comprising some or all CDRs entirely or substantially from a non-human donor immunoglobulin (e.g., a mouse or rat) and variable region framework sequences entirely or substantially from human immunoglobulin sequences. The non-human immunoglobulin providing the CDRs is called the "donor" and the human immunoglobulin providing the framework is called the "acceptor." In some instances, humanized antibodies may retain non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat) are identical between the respective CDRs. In particular variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least 85%, at least 90%, at least 95%, or 100% of corresponding residues defined by Kabat are identical. Hence, all parts of a humanized antibody, except possibly the CDRs, are entirely or substantially from corresponding parts of natural human immunoglobulin sequences.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

With regard to proteins as described herein, reference to amino acid residues corresponding to those specified by SEQ ID NO includes post-translational modifications of such residues.

The term "anti-CD33 antibody" refers to an antibody that specifically binds to the human CD33 protein. In a preferred embodiment the anti-CD33 antibody comprises the CDRs of the light chain variable region of SEQ ID NO:1 and the CDRs of the heavy chain variable region of SEQ ID NO:2. In another preferred embodiment, the anti-CD33 antibody comprises the light chain variable region of SEQ ID NO:1 and the heavy chain variable region of SEQ ID NO:2. In other preferred embodiments the anti-CD33 antibody includes a human constant region and is an IgG1 antibody.

An antibody-drug conjugate (ADC) is an antibody conjugated to a cytotoxic drug typically via a linker. The linker may comprise a cleavable unit or may be non-cleavable. Cleavable units include, for example, disulfide containing linkers that are cleavable through disulfide exchange, acid-labile linkers that are cleavable at acidic pH, and linkers that are cleavable by hydrolases, esterases, peptidases, and glucoronidases (e.g., peptide linkers and glucoronide linkers). Non-cleavable linkers are believed to release drug via a proteolytic antibody degradation mechanism.

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

The term "administration route" includes art-recognized administration routes for delivering a therapeutic protein such as, for example, parenterally, intravenously, intramuscularly, or subcutaneously. For administration of an ADC for the treatment of cancer, administration into the systemic circulation by intravenous or subcutaneous administration may be desired. For treatment of a cancer characterized by a solid tumor, administration can also be localized directly into the tumor, if so desired.

The term "treatment" refers to the administration of a therapeutic agent to a patient, who has a disease with the purpose to cure, heal, alleviate, delay, relieve, alter, remedy, ameliorate, improve or affect the disease.

The term "patient" includes human and other mammalian subjects that receive either prophylactic or therapeutic treatment.

The term "effective amount," "effective dose," or "effective dosage" refers to an amount that is sufficient to achieve or at least partially achieve the desired effect, e.g., sufficient to inhibit the occurrence or ameliorate one or more symptoms of a disease or disorder. An effective amount of a pharmaceutical composition is administered in an "effective regime." The term "effective regime" refers to a combination of amount of the composition being administered and dosage frequency adequate to accomplish prophylactic or therapeutic treatment of the disease or disorder.

The term "dosage unit form" (or "unit dosage form") as used herein refers to a physically discrete unit suitable as unitary dosages for a patient to be treated, each unit containing a predetermined quantity of active compound (an ADC in accordance with the present invention) calculated to produce the desired therapeutic effect in association with the required pharmaceutical carrier, diluent, or excipient. The specification for the dosage unit forms of the invention are dictated by and directly dependent on the unique characteristics of the active compound and the particular therapeutic effect to be achieved, and the limitations inherent in the art of compounding such an active compound for the treatment of patients.

Actual dosage levels of an ADC in a formulation of the present invention may be varied so as to obtain an amount of the ADC that is effective to achieve a desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well-known in the medical arts.

The phrase "pharmaceutically acceptable salt," as used herein, refers to pharmaceutically acceptable organic or inorganic salts of a compound. The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

A "cytotoxic effect" refers to the depletion, elimination and/or the killing of a target cell. A "cytotoxic agent" refers to an agent that has a cytotoxic effect on a cell.

A "cytostatic effect" refers to the inhibition of cell proliferation. A "cytostatic agent" refers to an agent that has a cytostatic effect on a cell, thereby inhibiting the growth and/or expansion of a specific subset of cells.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "pharmaceutical formulation" refers to a preparation which is in such form as to permit the biological activity of the active ingredient to be effective (when administered to a subject), and which contains no additional components which are unacceptably toxic to a subject to which the formulation would be administered. Such formulations are sterile.

Compositions or methods "comprising" one or more recited elements may include other elements not specifically recited.

Reference to a numerical range herein (e.g., "X to Y" or "from X to Y") includes the endpoints defining the range and all values falling within the range.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%."

DETAILED DESCRIPTION

This invention demonstrates optimal dosing of SGN-CD33A, a CD33-antibody drug conjugate (CD33-ADC), i.e., h2H12 antibody conjugated to a PBD, with cytarabine and an anthracycline antibiotic or an anthracenedione. Preferred anthracyclines include, e.g., daunorubicin, doxorubicin, idarubicin or mitoxantrone.

I. CD33 Antibody Drug Conjugates

A. Anti-CD33 Antibodies

The anti-CD33 antibody disclosed herein is the humanized 2H12 antibody (h2H12). The murine 2H12 antibody was raised in mice, using the human CD33 protein as an immunogen. After making hybridomas from the spleens of the immunized mice, followed by screening for CD33 binding activity, the murine 2H12 antibody was selected for humanization. The h2H12 antibody was derived from the murine 2H12 antibody. The humanization procedure is disclosed in PCT publication WO 2013/173,496; which is herein incorporated by reference for all purposes. The variable region sequences of the h2H12 light and heavy chains are provided as SEQ ID NO:1 and SEQ ID NO:2, respectively.

The h2H12 antibody comprises human constant regions. Sequences of human constant regions are provided in the sequence listing. The heavy chain constant region of h2H12 includes a substitution mutation, S239C, to facilitate conjugation of a drug-linker to the antibody. The sequence of a human constant region comprising the S239C mutation is provided at SEQ ID NOs:6 and 7. The h2H12 antibody comprising the S239C mutation is also referred to as h2H12EC.

B. Drug Linkers

Exemplary CD33 antibody-drug conjugates include PBD based antibody-drug conjugates; i.e., antibody-drug conjugates wherein the drug component is a PBD drug.

PBDs are of the general structure:

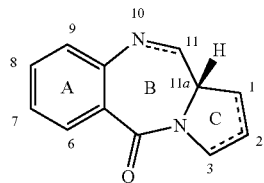

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, *In Antibiotics III*. Springer-Verlag, New York, pp. 3-11 (1975); Hurley and Needham-VanDevanter, *Acc. Chem. Res.*, 19, 230-237 (1986)). The ability of PBDs to form an adduct in the minor groove enables them to interfere with DNA processing, hence their use as anti-tumor agents.

The biological activity of these molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity.

In some embodiments, PBD based antibody-drug conjugates comprise a PBD dimer linked to an anti-CD33 antibody. The monomers that form the PBD dimer can be the same or different, i.e., symmetrical or unsymmetrical. The PBD dimer can be linked to the anti-CD33 antibody at any position suitable for conjugation to a linker. For example, in some embodiments, the PBD dimer will have a substituent at the C2 position that provides an anchor for linking the compound to the anti-CD33 antibody. In alternative embodiments, the N10 position of the PBD dimer will provide the anchor for linking the compound to the anti-CD33 antibody.

Typically the PBD based antibody-drug conjugate comprises a linker between the PBD drug and the anti-CD33 antibody. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in International Application No. WO 2011/130613 and is as follows wherein the wavy line indicates the site of attachment to the linker:

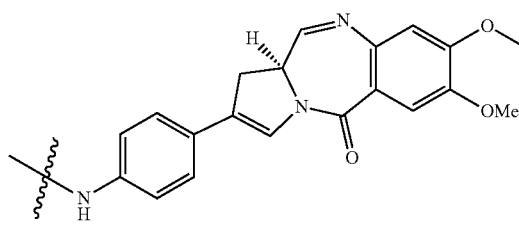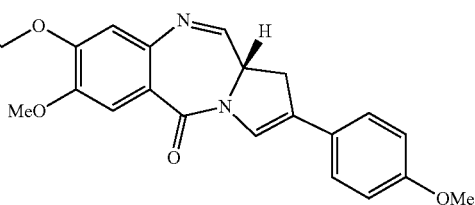

or a pharmaceutically acceptable salt thereof. An exemplary linker is as follows wherein the wavy line indicates the site of attachment to the drug and the antibody is linked via the maleimide group.

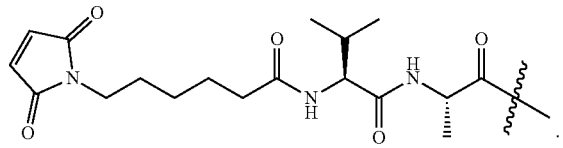 [SMILES: *C(=O)[C@H](C)NC(=O)[C@@H](NC(=O)CCCCCN1C(=O)C=CC1=O)C(C)C]

Exemplary PBDs based antibody-drug conjugates include antibody-drug conjugates as shown below wherein Ab is an antibody as described herein:

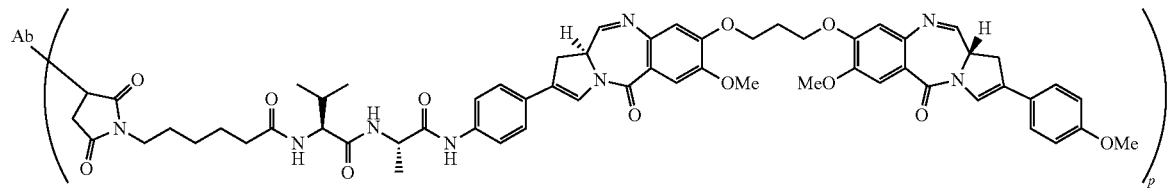

or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the drug linker via a sulfur atom of a cysteine residue that is engineered into the antibody. In some aspects, the cysteine residue is engineered into the antibody at position 239 (IgG1) as determined by the EU index (Kabat, Sequences of Proteins of Immunological Interest (National Institutes of Health, Bethesda, Md., 1987 and 1991).

C. CD33-ADCs

As used herein a "CD33-ADC" refers to an ADC that comprises an h2H12 antibody conjugated to a PBD molecule. The antibody portion comprises the variable light chain region of SEQ ID NO:1 and the variable heavy chain region of SEQ ID NO:2. The constant region is a human IgG1 constant region. The heavy chain constant region has a substitution mutation at amino acid 239 using Kabat numbering, i.e., S239C. The cysteine residue at position 239 is the point of attachment for the PBD molecule. The structure of the antibody, the linker and the PBD molecule is shown above. Methods to make the CD33-ADC are disclosed in PCT publication WO 2013/173,496 and PCT publication WO 2011/130613, both of which are incorporated by reference for all purposes.

II. 7 Plus 3 Chemotherapy

AML is frequently treated with first line induction therapy known as "7 plus 3". 7 plus 3 refers to the duration of the chemotherapy, i.e., seven days of standard-dose cytarabine, and three days of an anthracycline antibiotic or an anthracenedione. Preferred anthracyclines include, e.g., daunorubicin, doxorubicin, idarubicin or mitoxantrone. After blood count recovery, consolidation therapy follows with up to four consolidation cycles of seven days duration. Consolidation therapy includes administration of cytarabine and the CD33-ADC. Maintenance therapy can follow the induction-consolidation regimen. Maintenance therapy includes administration of the CD33-ADC.

III. Treatment of Acute Myeloid Leukemia (AML)

CD33-ADCs in combination with 7+3 induction-consolidation therapy can be used to treat acute myeloid leukemia (AML), preferably AML that has detectable levels of CD33 measured at either the protein (e.g., by immunoassay using one of the exemplified antibodies) or mRNA level. Some such AML cells show elevated levels of CD33 relative to noncancerous tissue of the same type, preferably from the same patient. An exemplary level of CD33 on AML samples amenable to treatment is 5000-150000 CD33 molecules per cell, although higher or lower levels can be treated. Optionally, a level of CD33 in a cancer is measured before performing treatment.

The combination of CD33-ADC with 7+3 induction-consolidation therapy can be applied to patients who are treatment naïve, who are refractory to conventional treatments (e.g., chemotherapy), or who have relapsed following a response to such treatments. Some cancer cells develop resistance to a therapeutic agent after increasing expression of a protein increases efflux of the therapeutic agent out of the cancer cell. Such proteins include P-glycoprotein, multidrug resistance-associated protein, lung resistance-related protein, and breast cancer resistance protein. Detection of drug resistance in cancer cells can be performed by those of skill. Antibodies or assays that detect efflux proteins are commercially available from, e.g., Promega, Millipore, Abcam, and Sigma-Aldrich. In one embodiment, a CD33-ADC in combination with a hypomethylating agent is used to treat a subject with a multi-drug resistant, CD33-positive AML.

In some embodiments the combination of a CD33-ADC with 7+3 induction-consolidation therapy is used to treat younger, fit patients who are able to withstand the toxicities associated with induction chemotherapy. These patients are often younger than 65, however patients with younger physiologic age who are older than age 65 may also receive induction therapy with a CD33-ADC with 7+3. In some embodiments, the CD33-ADC with 7+3 induction-consolidation therapy is administered to patients younger than 65 years old.

IV. Dosage and Administration

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, antibodies can be in lyophilized form for constitution with a suitable vehicle, e.g., sterile pyrogen-free water, before use. Formulations for the CD33-ADC comprising h2H12 antibody and a PBD molecule are disclosed e.g., at PCT/US2014/024466.

The CD33-ADC is administered intravenously, as is cytarabine, and the anthracycline antibiotic, e.g., daunorubicin, doxorubicin, idarubicin or mitoxantrone.

The combination of the CD33-ADC with 7+3 induction-consolidation therapy is dosed using an induction period followed by a consolidation period. In one embodiment, the induction period is seven days. The CD33-ADC is administered on induction days 1 and 4 at 10 µg/kg or 20 µg/kg; cytarabine is administered at 100 mg/m²/day on induction days 1-7, and daunorubicin is administered at 60 mg/m²/day on induction days 1-3. The consolidation period includes up to four cycles of seven days. The CD33-ADC is administered on consolidation day 1 at 10 µg/kg or 20 µg/kg; cytarabine is administered at 3 gm/m²/day on consolidation days 1, 3, and 5. The number of consolidation cycles is determined by the physician.

The combination of the CD33-ADC with 7+3 induction-consolidation therapy is dosed using an induction period followed by a consolidation period. In one embodiment, the induction period is seven days. The CD33-ADC is administered on induction day 1 at 30 µg/kg or 40 µg/kg; cytarabine is administered at 100 mg/m²/day on induction days 1-7, and daunorubicin is administered at 60 mg/m²/day on induction days 1-3. The consolidation period includes up to four cycles of seven days. The CD33-ADC is administered on consolidation day 1 at 10 µg/kg or 20 µg/kg; cytarabine is administered at 3 gm/m²/day on consolidation days 1, 3, and 5. The number of consolidation cycles is determined by the physician.

In another embodiment, the induction period is seven days. The CD33-ADC is administered on induction day 1 or induction day 4 at 10 µg/kg or 20 µg/kg; cytarabine is administered at 100 mg/m²/day on induction days 1-7, and daunorubicin is administered at 60 mg/m²/day on induction days 1-3. The consolidation period includes up to four cycles of seven days. The CD33-ADC is administered on consolidation day 1 at 10 µg/kg or 20 µg/kg; cytarabine is administered at 3 gm/m²/day on consolidation days 1, 3, and 5. The number of consolidation cycles is determined by the physician.

In a further embodiment, the induction period is seven days. The CD33-ADC is administered on induction days 1 and 4 at 10 µg/kg or 20 µg/kg; cytarabine is administered at 100 mg/m²/day on induction days 1-7, and idarubicin is administered at 12 mg/m²/day on induction days 1-3. The consolidation period includes up to four cycles of seven days. The CD33-ADC is administered on consolidation day 1 at 10 µg/kg or 20 µg/kg; cytarabine is administered at 3 gm/m²/day on consolidation days 1, 3, and 5. The number of consolidation cycles is determined by the physician.

The combination of the CD33-ADC with 7+3 induction therapy is dosed using an induction period. In one embodiment, the induction period is seven days. The CD33-ADC is administered on induction day 1 at 20 µg/kg and induction day 4 at 10 µg/kg; cytarabine is administered at 100 mg/m²/day on induction days 1-7, and daunorubicin is administered at 60 mg/m²/day on induction days 1-3.

The combination of the CD33-ADC with 7+3 induction therapy is dosed using an induction period. In one embodiment, the induction period is seven days. The CD33-ADC is administered on induction day 1 at 30 or 40 µg/kg; cytarabine is administered at 100 mg/m²/day on induction days 1-7, and daunorubicin is administered at 60 mg/m²/day on induction days 1-3.

An induction-consolidation regimen can be followed by maintenance dosing of the CD33-ADC. The maintenance dose of the CD33-ADC is typically given in forty-two day cycles for up to eight cycles. The CD33 ADC is administered at 5 µg/kg on day one of the cycle. The number of maintenance cycles is determined by the physician.

EXAMPLES

The following examples are offered to illustrate, but not to limit the claimed invention.

Example 1

CD33-ADC in Combination with 7+3 Chemotherapy for Treatment of Patients with AML Methods A combination of a CD33-ADC with a standard induction therapy is administered to patients with AML. The seven day induction period includes administration of cytarabine at 100 mg/m²/day on induction days 1-7, administration of the CD33-ADC on induction day 1 at 10 µg/kg or 20 µg/kg, and daunorubicin is administered at 60 mg/m²/day on induction days 1-3. A consolidation period of up to four cycles of seven days follows the induction period. The consolidation period includes administration of the CD33-ADC is on consolidation day 1 at 10 µg/kg or 20 µg/kg; cytarabine is administered at 3 gm/m²/day on consolidation days 1, 3, and 5. The consolidation period is followed by a maintenance period of forty-two day cycles for up to eight cycles. The CD33-ADC is administered at 5 µg/kg on day one of the maintenance cycle. Patients with clinical benefit may continue treatment until relapse or unacceptable toxicity. Investigator assessment of response is per IWG criteria; CRi requires either platelet count of ≥100,000/µL or neutrophils of ≥1,000/µL (Cheson 2003).

A combination of a CD33-ADC with a standard induction therapy is administered to patients with AML. The seven day induction period includes administration of cytarabine at 100 mg/m²/day on induction days 1-7, administration of the CD33-ADC on induction day 4 at 10 µg/kg or 20 µg/kg, and daunorubicin is administered at 60 mg/m²/day on induction days 1-3. A consolidation period of up to four cycles of seven days follows the induction period. The consolidation period includes administration of the CD33-ADC is on consolidation day 1 at 10 µg/kg or 20 µg/kg; cytarabine is administered at 3 gm/m²/day on consolidation days 1, 3, and 5. The consolidation period is followed by a maintenance period of forty-two day cycles for up to eight cycles. The CD33 ADC is administered at 5 µg/kg on day one of the maintenance cycle. Patients with clinical benefit may continue treatment until relapse or unacceptable toxicity. Investigator assessment of response is per IWG criteria; CRi requires either platelet count of ≥100,000/µL or neutrophils of ≥1,000/µL (Cheson 2003).

A combination of a CD33-ADC with a standard induction therapy is administered to patients with AML. The seven day induction period includes administration of cytarabine at 100 mg/m²/day on induction days 1-7, administration of the CD33-ADC on induction days 1 and 4 at 10 µg/kg or 20 µg/kg, and idarubicin is administered at 12 mg/m²/day on induction days 1-3. A consolidation period of up to four cycles of seven days follows the induction period. The consolidation period includes administration of the CD33-ADC is on consolidation day 1 at 10 µg/kg or 20 µg/kg; cytarabine is administered at 3 gm/m²/day on consolidation days 1, 3, and 5. The consolidation period is followed by a maintenance period of forty-two day cycles for up to eight cycles. The CD33 ADC is administered at 5 µg/kg on day one of the maintenance cycle. Patients with clinical benefit may continue treatment until relapse or unacceptable toxicity. Investigator assessment of response is per IWG criteria; CRi requires either platelet count of ≥100,000/µL or neutrophils of ≥1,000/µL (Cheson 2003).

A combination of a CD33-ADC with a standard induction therapy is administered to patients with AML. The seven day induction period includes administration of cytarabine at 100 mg/m²/day on induction days 1-7, administration of the CD33-ADC on induction day 1 at 30 µg/kg or 40 µg/kg, and daunorubicin is administered at 60 mg/m²/day on induction days 1-3. A consolidation period of up to four cycles of seven days follows the induction period. The consolidation period includes administration of the CD33-ADC is on consolidation day 1 at 10 µg/kg or 20 µg/kg; cytarabine is administered at 3 gm/m²/day on consolidation days 1, 3, and 5. The consolidation period is followed by a maintenance period of forty-two day cycles for up to eight cycles. The CD33-ADC is administered at 5 µg/kg on day one of the maintenance cycle. Patients with clinical benefit may continue treatment until relapse or unacceptable toxicity. Investigator assessment of response is per IWG criteria; CRi requires either platelet count of ≥100,000/µL or neutrophils of ≥1,000/µL (Cheson 2003).

Split-dose cohort: 42 patients (med age 45.5 yrs [range, 18-65]) were treated with 33A on D1 and 4 (10+10 [n=4] or 20+10 [n=38] mcg/kg) with 7+3. Most patients had intermediate (50%) or adverse (36%) cytogenetic risk (MRC) and 19% had secondary AML. 2 patients had hematologic DLTs (lack of recovery of platelets [25K] and/or ANC [500] by D42) and 20+10 mcg/kg was determined to be MTD. All patients had G4 myelosuppression, and the med time to count recovery from D1 of therapy in patients who achieved CR/CRi was 4.9 wks for neutrophils (≥1K) and 5.1 wks for platelets (≥100K). No non-hematologic treatment-emergent adverse events (TEAEs)≥G3 were reported in >10% of patients; non-hematologic TEAEs of any grade occurring in >20% of patients were nausea (62%), diarrhea, constipation (38% each), headache, hypokalemia (24% each), decreased appetite, fatigue, hypertension, and stomatitis (21% each). Of the 42 efficacy evaluable (EE) patients, best responses include 25 CR (60%), 7 CRi (17%), and 5 morphologic leukemia-free state (mLFS; 12%) with a CR+CRi (CRc) rate of 76%; 23 of 25 (94%) of responses were achieved with 1 cycle of therapy. Of the patients who achieved blast clearance (CR+CRi+mLFS), 77% (27/35) achieved an MRD negative status.

Single-dose cohort: To date, 25 patients (med age 58 yrs [range, 38-65]) were treated with 33A dosed on D1 (30 [n=14] or 40 [n=11] mcg/kg) with 7+3. Patients had intermediate (48%) or adverse (36%) cytogenetic risk and 16% had secondary AML. All patients had G4 myelosuppression and the med time to count recovery from D1 of therapy was 4.1 wks for neutrophils (≥1K) and 5.9 wks for platelets (≥100K) in patients who achieved CR/CRi. 2 patients had hematologic DLTs, 1 each at 30 and 40 mcg/kg. No non-hematologic TEAEs≥G3 were reported in >10% of patients and non-hematologic TEAEs were consistent with those seen in the D1 and 4 schedule. Of the 23 EE patients, best responses include 11 CR (46%), 6 CRi (25%), and 4 mLFS (17%) with a CRc rate of 71%; all responses were achieved with 1 cycle of therapy. Of the patients who achieved blast clearance, 89% (17/19) achieved a MRD negative status.

Across schedules (N=67), the CRc rate was 72% and 79% (44/56) patients with blast clearance achieved MRD negativity. The 30- and 60-day mortality rates were 1% and 7%, respectively. Median OS is not yet reached for either schedule and 52 patients (78%) were alive at the time of this analysis. Total exposure to 33A was characterized for the different dosing regimens and pharmacokinetic data demonstrate rapid elimination of 33A.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating CD33 expressing acute myeloid leukemia (AML) in a subject in need of such treatment, the method comprising:

1) administering an anthracycline antibiotic, and a CD33 antibody drug conjugate (ADC) in an induction period of seven days, wherein the CD33-ADC comprises a humanized 2H12 antibody and a PBD cytotoxic agent, and wherein 10 µg/kg or 20 µg/kg of the CD33-ADC is administered on day one of the induction period and 10 µg/kg of the CD33-ADC is administered on day four of the induction period;

wherein the anthracycline antibiotic: 1) is cytarabine and is administered on induction days 1-7; or 2) is daunorubicin and is administered on induction days 1-3; and 2) after the induction period, administering the CD33-ADC and cytarabine in up to four consolidation cycles each comprising seven days, wherein the CD33-ADC is administered on day 1 of each consolidations cycle at 10 µg/kg or 20 µg/kg, and wherein cytarabine is administered on days 1, 3, and 5 of each consolidation cycles at 3 mg/m$^2$/day.

2. The method of claim 1, wherein the PBD cytotoxic agent has the formula

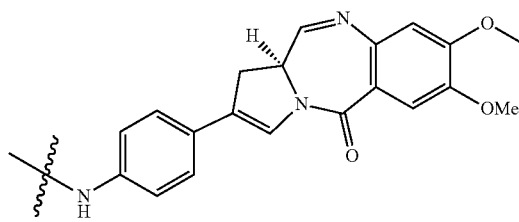
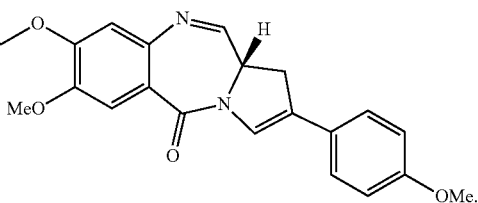

3. The method of claim 1, wherein the anthracycline antibiotic is daunorubicin and is administered at 60 mg/m$^2$/day on induction days 1-3.

4. The method of claim 1, wherein the anthracycline antibiotic is cytarabine and is administered at 100 mg/m$^2$/day on induction days 1-7.

5. The method of claim 1, wherein the humanized 2H12 antibody comprises a light chain variable region of SEQ ID NO:1 and a heavy chain variable region of SEQ ID NO:2.

6. A method of treating CD33 expressing acute myeloid leukemia (AML) in a subject in need of such treatment, the method comprising:
1) administering an anthracycline antibiotic, and a CD33 antibody drug conjugate (ADC) in an induction period of seven days, wherein the CD33-ADC comprises a humanized 2H12 antibody and a PBD cytotoxic agent, and wherein 30 μg/kg or 40 μg/kg of the CD33-ADC is administered on day one of the induction period;
wherein the anthracycline antibiotic: 1) is cytarabine and is administered on induction days 1-7; or 2) is daunorubicin and is administered on induction days 1-3; and
2) after the induction period, administering the CD33-ADC and cytarabine in up to four consolidation cycles each comprising seven days, wherein the CD33-ADC is administered on day 1 of each consolidations cycle at 10 μg/kg or 20 μg/kg, and wherein cytarabine is administered on days 1, 3, and 5 of each consolidation cycles at 3 mg/m$^2$/day.

7. The method of claim 6, wherein the PBD cytotoxic agent has the formula

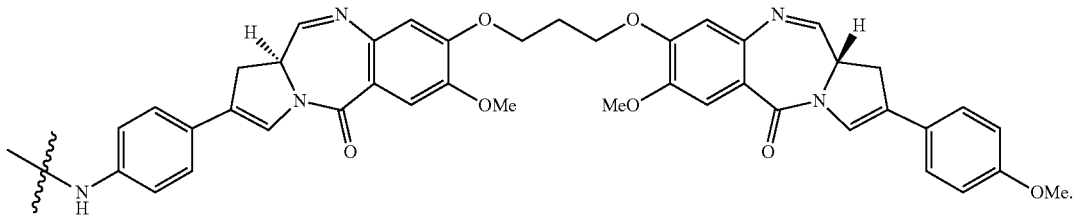 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

8. The method of claim 6, wherein the anthracycline antibiotic is daunorubicin and is administered at 60 mg/m$^2$/day on induction days 1-3.

9. The method of claim 6, wherein the anthracycline antibiotic is cytarabine and is administered at 100 mg/m$^2$/day on induction days 1-7.

10. The method of claim 6, wherein the humanized 2H12 antibody comprises a light chain variable region of SEQ ID NO:1 and a heavy chain variable region of SEQ ID NO:2.

11. The method of claim 1, wherein the method further comprising, after the consolidation cycles, administering the CD33-ADC in up to eight maintenance cycles each comprising forty two days, wherein the CD33-ADC is administered at 5 μg/kg on day 1 of each maintenance cycle.

12. The method of claim 6, wherein the method further comprising, after the consolidation cycles, administering the CD33-ADC in up to eight maintenance cycles each comprising forty two days, wherein the CD33-ADC is administered at 5 μg/kg on day 1 of each maintenance cycle.

\* \* \* \* \*

SEQUENCE LISTING

<160> NUMBER OF SEQ ID NOS: 7

<210> SEQ ID NO 1
<211> LENGTH: 107
<212> TYPE: PRT
<213> ORGANISM: Artificial Sequence
<220> FEATURE:
<223> OTHER INFORMATION: 2H12 LG  Light chain variable region

<400> SEQUENCE: 1

Asp Ile Gln Met Thr Gln Ser Pro Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
            35                  40                  45

Tyr Arg Ala Asn Arg Leu Val Asp Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 2
<211> LENGTH: 117
<212> TYPE: PRT
<213> ORGANISM: Artificial Sequence
<220> FEATURE:
<223> OTHER INFORMATION: 2H12 HI  Heavy chain variable region

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
            35                  40                  45

Gly Trp Ile Tyr Pro Gly Asp Gly Ser Thr Lys Tyr Asn Glu Lys Phe
50                  55                  60

Lys Ala Lys Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser
            115

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 329
<212> TYPE: PRT
<213> ORGANISM: Homo sapiens

<400> SEQUENCE: 5

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys

-continued

```
                1               5                   10                  15
            Ser Thr Ser Gly Gly Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Gln Thr
            65                      70                  75                  80

Tyr Ile Cys Asn Val Asn His Lys Pro Ser Asn Thr Lys Val Asp Lys
                            85                  90                  95

Lys Val Glu Pro Lys Ser Cys Asp Lys Thr His Thr Cys Pro Pro Cys
                        100                 105                 110

Pro Ala Pro Glu Leu Leu Gly Gly Pro Cys Val Phe Leu Phe Pro Pro
                        115                 120                 125

Lys Pro Lys Asp Thr Leu Met Ile Ser Arg Thr Pro Glu Val Thr Cys
                    130                 135                 140

Val Val Val Asp Val Ser His Glu Asp Pro Glu Val Lys Phe Asn Trp
            145                     150                 155                 160

Tyr Val Asp Gly Val Glu Val His Asn Ala Lys Thr Lys Pro Arg Glu
                            165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Asp Glu
            225                     230                 235                 240

Leu Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
            305                     310                 315                 320

Gln Lys Ser Leu Ser Leu Ser Pro Gly Lys
                            325                 330

<210> SEQ ID NO 7
<211> LENGTH: 329
<212> TYPE: PRT
<213> ORGANISM: Homo sapiens

<400> SEQUENCE: 7
```

-continued

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20              25              30
Phe Pro Glu Pro Val Thr Val Ser Trp Asn Ser Gly Ala Leu Thr Ser
            35              40              45
Gly Val His Thr Phe Pro Ala Val Leu Gln Ser Ser Gly Leu Tyr Ser
        50              55              60
Leu Ser Ser Val Val Thr Val Pro Ser Ser Ser Leu Gly Thr Gln Thr
65              70              75                      80
Tyr Ile Cys Asn Val Asn His Lys Pro Ser Asn Thr Lys Val Asp Lys
                85              90              95
Lys Val Glu Pro Lys Ser Cys Asp Lys Thr His Thr Cys Pro Pro Cys
            100             105             110
Pro Ala Pro Glu Leu Leu Gly Gly Pro Cys Val Phe Leu Phe Pro Pro
        115             120             125
Lys Pro Lys Asp Thr Leu Met Ile Ser Arg Thr Pro Glu Val Thr Cys
        130             135             140
Val Val Val Asp Val Ser His Glu Asp Pro Glu Val Lys Phe Asn Trp
145             150             155             160
Tyr Val Asp Gly Val Glu Val His Asn Ala Lys Thr Lys Pro Arg Glu
                165             170             175
Glu Gln Tyr Asn Ser Thr Tyr Arg Val Val Ser Val Leu Thr Val Leu
            180             185             190
His Gln Asp Trp Leu Asn Gly Lys Glu Tyr Lys Cys Lys Val Ser Asn
        195             200             205
Lys Ala Leu Pro Ala Pro Ile Glu Lys Thr Ile Ser Lys Ala Lys Gly
        210             215             220
Gln Pro Arg Glu Pro Gln Val Tyr Thr Leu Pro Pro Ser Arg Asp Glu
225             230             235             240
Leu Thr Lys Asn Gln Val Ser Leu Thr Cys Leu Val Lys Gly Phe Tyr
                245             250             255
Pro Ser Asp Ile Ala Val Glu Trp Glu Ser Asn Gly Gln Pro Glu Asn
            260             265             270
Asn Tyr Lys Thr Thr Pro Pro Val Leu Asp Ser Asp Gly Ser Phe Phe
        275             280             285
Leu Tyr Ser Lys Leu Thr Val Asp Lys Ser Arg Trp Gln Gln Gly Asn
        290             295             300
Val Phe Ser Cys Ser Val Met His Glu Ala Leu His Asn His Tyr Thr
305             310             315             320
Gln Lys Ser Leu Ser Leu Ser Pro Gly
                325
```